US005614515A

United States Patent [19]
Rodgers et al.

[11] Patent Number: 5,614,515
[45] Date of Patent: Mar. 25, 1997

[54] LAZAROID-BASED COMPOSITIONS AND METHOD FOR PREVENTING ADHESION FORMATION USING THE SAME

[75] Inventors: Kathleen E. Rodgers, Long Beach; Gere S. Dizerega, Pasadena, both of Calif.

[73] Assignee: University of Southern California, Los Angeles, Calif.

[21] Appl. No.: 341,651

[22] Filed: Nov. 17, 1994

[51] Int. Cl.$^6$ .......................... A61K 31/56; A61K 31/495
[52] U.S. Cl. ............................................. 514/176; 514/249
[58] Field of Search .................................... 514/169, 176, 514/249

[56] References Cited

U.S. PATENT DOCUMENTS

| | | | |
|---|---|---|---|
| 4,937,254 | 6/1990 | Sheffield et al. | 514/420 |
| 4,968,675 | 11/1990 | Su et al. | 514/176 |
| 5,256,408 | 10/1993 | Babcock et al. | 424/78.04 |

FOREIGN PATENT DOCUMENTS

| | | |
|---|---|---|
| WO87/01706 | 3/1987 | WIPO. |
| WO91/19482 | 12/1991 | WIPO. |

OTHER PUBLICATIONS diZerega & Rodgers (1992), "Prevention of Postoperative Adhesions" in The Peritoneum, diZerega, G. S. & Rodgers K. E., ed., Springer–Verlag, New York, pp. 307–369.
Elkins, T. E. (1990), "Can a Pro–Coagulant Substance Prevent Adhesions?" in Treatment of Post–Surgical Adhesions, diZerega, G. S. et al. eds., Wiley–Liss, New York, pp. 103–112.
Rodgers, K. E. (1990), "Nonsteroidal anti–inflammatory drugs (NSAIDs) in the treatment of Postsurgical adhesion," in Treatment of Post–Surgical Adhesiona, diZerega, G. S. et al., eds., Wiley–Liss, New York, pp. 119–129.
Thomas et al. (1993), Biochem. Pharmacol., vol. 45, pp. 241–251.
Braughler et al. (1987), J. Biol. Chem., vol. 262, pp. 10438–10440.
Fisher et al. (1991), Neurology, vol. 41, pp. 297–299.
Kim et al. (1992), Cancer Letters, vol. 64, pp. 61–66.
Singh and Bonin (1991), Life Sciences, vol. 49, pp. 2053–2058.
Braughler et al. (1989), Free Rad. Biol. & Med., vol. 7, pp. 125–130.
Braughler et al., (1989), Free Rad. Biol. & Med., vol. 6, pp. 289–301.
Aoki et al. (1990), J. Cardiovas. Pharm., vol. 15, pp. 205–210.
Hall et al. (1990), Stroke, vol. 21, 111–83–87.
Kim et al. (1993), Cancer Chemother. Pharmacol., vol. 33, pp. 187–190.
Chatelut et al. (1993), Cancer Chemother. Pharmacol., vol. 32, pp. 179–182.
Shappell et al. (1992), FASEB Journal, vol. 6(4), p. A1428.
Choi et al. (1993), Am. J. Pathol., vol. 142, pp. 519–528.
Rodgers et al. (1988), Int'l. J. Immunopharm., vol. 10, pp. 111–120.
Lewis, D. H. (1990), "Controlled Release of Bioactive Agents from Lactide/Glycolide Polymers," in Biodegradable Polymers as Drug Delivery Systems, Jason & Langer, ed., pp. 1–41.
Hoeckel et al. (1987), Annales Chirurgiae et Gynaecologiae, vol. 76, pp. 306–313.
Rodgers et al. (1990), Int. J. Fertil., vol. 35, p. 40.
Abe et al. (1990), J. Surg. Res., vol. 49, p. 322.
Fertility & Sterility, vol. 51, p. 933, 1989.
Diamond et al. (1991), Fertility and Sterility, vol. 55, p. 389.
Diamond et al. (1991), J. Gyn. Surg., vol. 7, p. 1.
Nishimura et al. (1984), Am. J. Med., vol. 77, pp. 102–106.
Hall, E. D. (1992), Ann. Neuro., vol. 32, pp. 137–142.

Primary Examiner—Marianne M. Cintins
Assistant Examiner—Keith MacMillan
Attorney, Agent, or Firm—Banner & Witcoff, Ltd.

[57] ABSTRACT

Compositions and method for the minimization or prevention of adhesion formation, whereby an effective amount of at least one lazaroid compound, preferably one of general formula I, is administered for a period of time sufficient to permit tissue repair. The compound of general formulae I or II is preferably administered in conjunction with a delivery vehicle (e.g., microcapsules, microspheres, biodegradable polymer films, lipid-based delivery systems such as liposomes and lipid foams, viscous instillates and absorbable mechanical barriers) useful for maintaining local concentrations of the compound at an effective level.

22 Claims, No Drawings

LAZAROID-BASED COMPOSITIONS AND METHOD FOR PREVENTING ADHESION FORMATION USING THE SAME

FIELD OF THE INVENTION

The present invention relates to compositions comprising lazaroids thereof and their use in a method for preventing post-operative adhesion formation between organ surfaces.

BACKGROUND OF THE INVENTION

Adhesion formation, in particular following peritoneal surgery, is a major source of postoperative morbidity and mortality. Appendectomy and gynecologic surgery are the most frequent surgical procedures implicated in clinically significant adhesion formation. The most serious complication of intraperitoneal adhesions is intestinal obstruction; in addition, adhesions are associated with chronic or recurrent pelvic pain and infertility in females.

The pathogenesis of adhesion formation is complex and not entirely understood. The first step is believed to involve excess fibrin deposition to form a scaffold. Organization of the fibrin scaffold by cellular elements, including fibroblasts and mesothelial cells, then follows.

Various approaches for the prevention of adhesion formation have been actively explored [diZerega, G. S. & Rodgers, K. E., "Prevention of Postoperative Adhesions," in "The Peritoneum," diZerega, G. S. & Rodgers, K. E., eds., Springer-Verlag, New York, pp. 307–369 (1992)]. In general, the treatments fall into three categories: prevention of fibrin deposition in the peritoneal exudate, reduction of local tissue inflammation; and removal of fibrin deposits.

Therapeutic attempts to prevent fibrin deposition include peritoneal lavages to dilute or wash away fibrinous exudate, surgical techniques to minimize tissue ischemia and introduction of barriers to limit apposition of healing serosal surfaces. Although the use of agents affecting coagulation of the fibrinous fluid has also been proposed, results obtained to date suggest that the use of procoagulants in areas of substantial bleeding may actually promote adhesion formation [Elkins, T. E., "Can a Pro-Coagulant Substance Prevent Adhesions?" in "Treatment of Post-Surgical Adhesions," diZerega, G. S. et al., eds., Wiley-Liss, New York, pp. 103–112 (1990)].

Physical barriers have been used in attempts to prevent adhesion formation by limiting tissue apposition during the critical period of peritoneal healing, thereby minimizing the development of fibrin matrix between tissue surfaces. Barrier agents which have been employed include both mechanical barriers and viscous solutions. Mixed results have been obtained using a barrier comprising a thin sheet of expanded poly-tetrafluoroethylene; in any event, such a membrane is less than ideal, as it must be sutured into place and is nonabsorbable. While an absorbable barrier (for example, a barrier made of oxidized regenerated cellulose) would be preferable, not all studies have demonstrated the efficacy of such barriers in preventing adhesions. Liquid barriers have also been considered for use in preventing adhesions; for example, chondroitin sulfate and carboxymethyl cellulose have both shown some promise in animal models. In addition, solution of dextran 70 (molecular weight=70,000) have been the subject of a number of clinical studies. Not all clinical evaluations of 32% dextran 70 have found a therapeutic effect, however, and the clinical use of the solution is also associated with clinically important side effects.

Anti-inflammatory drugs have been evaluated for their effects on postoperative adhesion formation, as they may limit the release of fibrinous exudate in response to inflammation at the surgical site. Two general classes of these drugs were tested: cortico-steroids and nonsteroidal anti-inflammatory drugs. The results of corticosteroid use in animal studies have generally not been encouraging, and clinical use of corticosteroids is limited by their other pharmacologic properties. While experimental evaluations of nonsteroidal anti-inflammatory drugs in postoperative adhesion formation show promise [Rodgers, K. E., "Non-steroidal anti-inflammatory drugs (NSAIDs) in the treatment of Postsurgical adhesion," in "Treatment of Post-Surgical Adhesions," diZerega, G. S. et al., eds., Wiley-Liss, New York, pp. 119–129 (1990)], clinical evaluations of these drugs for adhesion prevention is needed.

The third approach explored to date involves the removal of fibrin deposits. Although proteolytic enzymes (e.g., pepsin, trypsin and papain) should theoretically augment the local fibrinolytic system and limit adhesion formation, these enzymes are rapidly neutralized by peritoneal exudates rendering them virtually useless for adhesion prophylaxis. While various fibrinolytics (for example, fibrinolysin, streptokinase and urokinase) have been advocated, a potential complication to the clinical use of these enzymes in postoperative therapy is excessive bleeding resulting from their administration. Topical application of a recombinant tissue plasminogen activator (rt-PA) has been shown to reduce adhesion formation in a variety of animal models; further research is necessary to develop suitable delivery systems to provide this drug to the surgical site and identify the postoperative time when adhesion prevention is feasible.

To date, no single therapeutic approach has proven universally effective in preventing formation of postoperative intraperitoneal adhesions. Therefore, there is a need for compositions and methods which may be used safely and effectively to prevent adhesion formation in a variety of different contexts.

OBJECTS OF THE INVENTION

It is an object of the present invention to provide lazaroid-based compositions for use in preventing or minimizing adhesion formation.

It is another object of the invention to provide methods for the minimization or prevention of post-surgical adhesion formation employing compositions.

These and other objects of the invention will be apparent in light of the detailed description below.

SUMMARY OF THE INVENTION

The present invention relates to a method for the minimization or prevention of adhesion formation comprising administering to a subject an effective amount of a composition comprising at least lazaroid compound to effect tissue repair. Preferably, the composition includes at least one lazaroid compound of the general formula I:

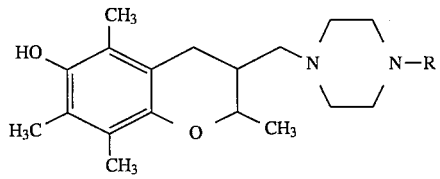

wherein R represents a formula:

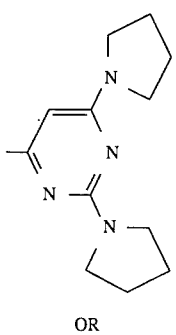

OR

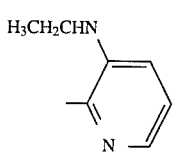

or formula II:

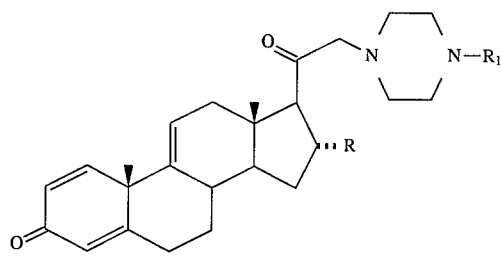

wherein R represents H or CH$_3$; R$_1$ represents formula Ia, as defined above, or formula IIa:

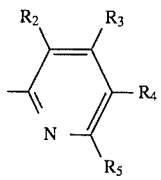

wherein R$_2$, R$_3$, R$_4$, and R$_5$ independently represent H or NR$_6$R$_7$ wherein R$_6$ and R$_7$ independently represent H and C$_1$–C$_6$ alkyl. The composition also includes a drug delivery system which maintains an effective concentration of the compound at a site of potential adhesion formation during the perioperative interval.

Pursuant to another aspect of the present invention, adhesion formation is minimized or prevented by administration of at least one lazaroid compound, preferably one of the general formulae I or II, at a site of potential adhesion formation for a period of time sufficient to permit substantial tissue repair (e.g., re-epithelialization or mesothelial repair) at the site.

DETAILED DESCRIPTION OF THE INVENTION

All literature references, patents and patent applications cited in this application are incorporated herein in their entirety.

The inventive composition and method are useful in minimizing or preventing formation of adhesions between organ surfaces (not cell-to-cell adhesion), the most common cause of which is prior surgery. The inventive composition and method have been shown to be especially effective in preventing adhesion formation in the peritoneum following surgery. In addition, the present invention finds utility in other contexts, e.g., for cardiovascular, orthopedic, thoracic, ophthalmic, CNS and other uses, where prevention of the formation of adhesions is a significant concern. For example, prevention of adhesion formation or drug loculation during the intraperitoneal administration of chemotherapeutic agent is contemplated as within the scope of the present invention. For the purposes of the following discussion, attention is directed primarily to description of compositions and methods useful in inhibiting peritoneal adhesion formation.

The present invention contemplates the use of a composition comprising at least one lazaroid compound. Suitable, but non-limiting, examples of lazaroids and their preparation for use in the invention include, for instance, the aminosteroids represented in WO 87/01706. Preferably, the composition includes at least one lazaroid compound of the general formula I:

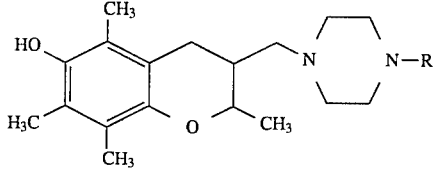

wherein R represents a formula:

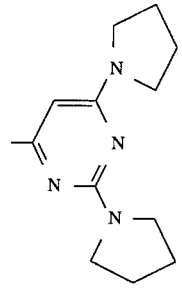

OR

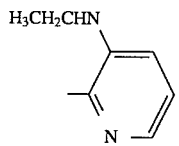

or formula II:

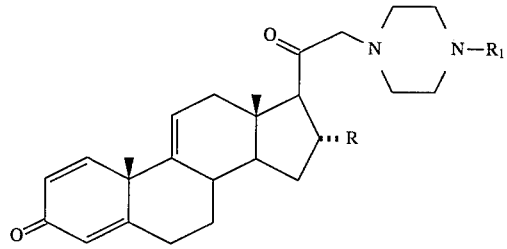

wherein R represents H or CH$_3$; R$_1$ represents formula Ia, as defined above, or formula IIa:

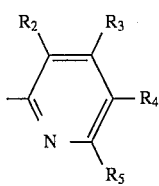

wherein $R_2$, $R_3$, $R_4$, and $R_5$ independently represent H or $NR_6R_7$ wherein $R_6$ and $R_7$ independently represent H and $C_1$-$C_6$ alkyl. The lazaroids are preferably used in a form of a pharmaceutically acceptable salt, hydrate or solvate such as the ones described in WO 87/01706 and U.S. Pat. No. 5,256,408.

A particularly preferred Formula I lazaroids for use in the invention are U83,836E ((−)-2-[[4-(2,6-Di-1-pyrrolindinyl-4-pyrimidinyl)-1-piperazinyl] methyl]-3,4-dihydro-2,5,7,8-tetramethyl-2H-1-benzopyran-6-ol, dihydrochloride); U-78517G (same as U-83836E except 2-hydroxy-1,2,3-propanetricarboxylate (1:2) salt form is used); U-78518E (2H-1-benzopyran-6-ol, 2-[[4-[3-(ethylamino)-2-pyridinyl]-1-piperazinyl]methyl]-3,4-dihydro-2,5,7,8-tetramethyl-, hydrochloride); U-78517F (a racemic mixture of U-83,836 and its enantiomer); and U-78518F (same as U-78518E except that the (Z)-2-butenedioate salt form is used), all produced by the UpJohn Company (Kalamazoo, Mich., USA).

Preferred formula II lazaroid compounds for use in the invention include U-74500A (pregna-1,4,9(11)-triene-3,20-dione, 21-[4-[5,6-bis(diethylamino)-2-pyridinyl]-1-piperazinyl]-16-methyl-, hydrochloride, (16.alpha.) -); U-75412E (21-[4-[3-ethylamino)-2-pyridinyl]-1-piperazinyl-16-methyl-pregna-1,4,9(11)-trien-3,20-dione, (16.alpha.)-(Z)-2-butenedioate (1:1)); U-75412A (same as U-75412E except the hydrochloride form is used); U-74006F (21-[4-(2,6-di-1-pyrrolidinyl-4-pyrimidinyl)-1-piperazinyl]-16-methyl-16.alpha.)-pregna-1,4,9(11)-triene-3,20-dione monomethanesulfonate; also known as tirilazad mesylate); U-74389G (21-(4-(2,6-di-1-pyrrolindinyl-4-pyrimidinyl)-1-piperazinyl]-pregna-1,4,9(11)-triene-3,20-dione, (Z)-2-butenedioate (1:1) ); U-74389F (same as U-74389G except that the monomethanesulfonate salt form is used); U-77372E (16-alpha-methyl-21-[4-[4,6-bis(2-pyridinyl)-1,3,5-triazin-2-yl]-1-piperazinyl]-pregna-1,4,9(11)-triene-3,20-dione, monomethanesulfonate); and U-78000E (16-alpha-methyl-21-[4-[2,6-bis(2-pyridinyl)-4-pyrimidinyl]-1-piperazinyl]-pregna-1,4,9(11)-triene-3,20-dione, monomethanesulfonate), all produced by the UpJohn Company (Kalamazoo, Mich., USA). These aminosteroids and methods for their preparation is described in WO 87/01706, published Mar. 26, 1987.

Other useful 21-aminosteroid lazaroids such as U-74915, U-75014E, and U-75013E and their syntheses are reported in J. M. Braughler et al. "Novel Membrane Localized Iron Chelators as Inhibitors of Iron-dependent Lipid Peroxidation," *Biochem. Pharm.*, Vol. 37, pp. 3853–60 (1988).

In addition, U-79206 (Ethanol, 2-[(2,6-di-1-pyrrolidinyl)-4-pyrimidinylmethylamino]) and U-76556 (4-[3-(ethylamino)-2-pyridinyl]piperazine), also produced by the UpJohn Company (Kalamazoo, Mich., USA), are also preferred in practicing the invention.

Lazaroids are a unique group of 21-aminosteroids and 2-methylaminochromans compounds which exert a protective effect against tissue damage after trauma and/or ischemia. See, e.g., P. D. Thomas et al. (1993) "Inhibition of Superoxide-generating NADPH Oxidase of Human Neutrophils by Lazaroids (21-aminosteroids and 2-methylaminochromans)," *Biochem. Pharmacol.*, Vol. 45, pp. 241–251); E. D. Hall (1992) "Novel Inhibitors of Iron-dependent Lipid Peroxidation for Neurodegenerative Disorders," *Ann. Neuro.*, Vol. 32 (Suppl.), pp. 137–42. In several animal models of traumatic and ischemic injury to the central nervous system, lazaroids have been shown to prevent secondary tissue injury associated with oxidative cell damage. E. D. Hall et al. (1992), ibid.

The protective effects of lazaroids have been attributed to their ability to inhibit lipid peroxidation reactions as well as reduce production of reactive oxygen metabolites (e.g., hydrogen peroxide and free radicals) by leukocytes and monocytes. See, e.g., J. M. Braughler et al. "Novel 21-Amino Steroids as Potent Inhibitors of Iron-dependent Lipid Peroxidation," *J. Biol. Chem.*, Vol. 262(22), pp. 10438–10440 (1987)). Lazaroids have been shown to inhibit the respiratory burst of neutrophils and monocytes. See, e.g., S. M. Shappell et al. "Inhibition of Neutrophil Beta-2-Integrin-mediated $H_2O_2$ production by Lazaroids U75412 and U78517," *FASEB J.* A1428; Fisher et al. "A 21-aminosteroid Inhibits Stimulated Monocyte Hydrogen Peroxide and Chemiluminescence Measurements form MS patients and Controls," *Neurology*, Vol. 41, pp 297–299 (1991); Fisher et at. "A 21-Aminosteroid Reduces Hydrogen Peroxide Generation by and Chemiluminescence of Stimulated Human Leukocytes," *Stroke*, Vol. 21, pp 1435–1438 (1990); P. D. Thomas et al, Ibid).

Lazaroids and related compounds where also found to inhibit cell proliferation in vitro. See, e.g., R. S. Kim et al. "Antiproliferative Properties of Aminosteroid Antioxidants on Cultured Cancer Cells," *Cancer Letters*, Vol. 64(1), pp 61–66 (1992); J. P. Singh et al. "Inhibition of Proliferation of Fibroblasts by Lazaroids (21-Aminosteroids)," *Life Sciences*, Vol. 49, pp. 2053–2058 (1991). However, a comparison of various lazaroids and other known antioxidants with similar antioxidant potential, e.g. vitamin E and Probucol, suggested that cell growth inhibition by lazaroids may be unrelated to their antioxidant activity. J. P. Singh et al. (1991), ibid.

While the present invention is not bound to any particular theory, it is believed that lazaroid compounds such as those of general formulae I and II (and in particular, U83,836e) may inhibit adhesion formation through a variety of mechanisms. For instance, reduction of lipid peroxidation after ischemia is thought to increase the fibrinolytic potential of the peritoneum and this may account for diminished adhesion formation. In addition, release of arachidonic acid from cells is blocked by these compounds due to membrane stabilizing effects, not inhibition of phospholipase $A_2$. See, e.g., J. M. Braughler et al. "The 21-aminosteroid Inhibitors of Lipid Peroxidation Reactions with Lipid Peroxyl and Phenoxyl Radicals," *Free Rad. Biol. & Med.*, Vol. 7, pp. 125–139 (1989); J. M. Braughler et al. "Central Nervous System Trauma and Stroke. I. Biochemical Considerations for Oxygen Radical Formation and Lipid Peroxidation," *Free Rad. Biol. & Med.*, Vol. 6, pp. 289–301 (1989); J. M. Braughler et al. "Novel Membrane Localized Iron Chelators as Inhibitors of Iron-dependent Lipid Peroxidation," *Biochem. Pharm.*, Vol. 37, pp. 3853–60 (1988); N. Aoki et al. "Protective Effects of a Novel Non-glucocorticoid 21-Aminosteroid (U74006F) during traumatic Shock in Rats," *J. Cardiovas. Pharm.*, Vol. 15, pp. 205–210 (1990); E. D. Hall et al. "Nonsteroidal Lazaroid U78517F in Models of Focal and Global Ischemia," *Stroke*, Vol. 21, III-83-7 (1990); M. Choi et al. "U75412E, a Lazaroid, Prevents Progressive Burn Ischemia in a Rat Burn Model," *Amer. J. Path.*, Vol. 142, pp. 519–528 (1993).

As is well recognized in the art, however, no one of these possible mechanisms of action of lazaroids, e.g., U83,836e and other compounds of general formulae I and II, would in and of itself be sufficient to enable one to predict whether these compounds would have any utility in reduction of adhesion formation.

For example, lazaroids inhibit the respiratory burst of neutrophils and monocytes. S. M. Shappell, "Inhibition of Neutrophil Beta-2-Integrin-mediated $H_2O_2$ Production by Lazaroids U75412 and U78517," *FASEB J.*, A1428; M. Fisher et al. (1991), supra; M. Fisher et al. (1990), supra; P. D. Thomas et al. (1993), supra. In contrast, tolmetin, a NSAID agent also shown to reduce adhesion formation, has been shown to increase the production of oxygen radicals by postoperative macrophages in rabbits (K. Rodgers et al. (1988) "Effects of rolmerin sodium dihydrate on normal and post-surgical peritoneal cell function," *Int'l. J. Immunopharm.*, Vol 10, pp. 111–120)). Moreover, lazaroids inhibit cellular proliferation which is believed to be necessary for re-epithelialization of the injured site and for prevention of adhesions. See, e.g., R. S. Kim et al. (1992), supra, and J. P. Singh et al (1991), supra.

Pursuant to the method of the present invention, at least one lazaroid compound, preferably one of general formulae I or II, is maintained in an effective concentration at the site of potential adhesion formation for a period of time sufficient to permit substantial re-epithelialization. The lazaroid compound is typically administered over the perioperative interval, which for purposes of the present invention may include time shortly prior to surgery through the surgery itself up to some time after completion of surgery. The term of administration may vary depending upon a number of factors which would be readily appreciated those skilled in the art. In general, administration of a composition in accordance with the present invention including at least one lazaroid compound should be effected from the time of surgery for at least 24 to 48 hours after completion of the surgical procedure. As healing is in most cases complete within about two weeks, it is generally not necessary to continue administration of a composition in accordance with the present invention much longer than two weeks. The composition in accordance with the present invention comprising at least one lazaroid compound is administered from about the time of surgery for a period ranging between about 24 hours and about 14 days, preferably ranging between about 24 hours and about 7 days and most preferably ranging between about 24 and about 72 hours.

The rate of administration of the lazaroid compound may be varied over a fairly broad range. The concentrations of the lazaroid compound I which can be administered would be limited by efficacy at the lower end and the solubility of the compound at the upper end. With respect to compositions comprising lazaroids, the concentration ranges are as follows:

| General Range | Preferred Range |
| --- | --- |
| 0.04 ng–0.2 mg/hr/kg | 0.04–40 µg/hr/kg |
| 0.007 ng–0.033 mg /hr/cm$^2$ | 0.007–6.7 µg/hr/cm$^2$ |
| 0.0027 ng–0.013 mg /hr/cm$^2$/kg | 0.0027–2.67 µg/ hr/cm$^2$/kg |

As defined herein, kg refers to body weight of the subject and cm$^2$ refers to the surface area of the injury site to be treated. The wt/hr/cm$^2$ ranges are generally used for intercavitary administration of lazaroid compounds with liquid or barrier delivery systems.

The lazaroid compound may be administered directly in a suitable vehicle, e.g., a solution of citric acid, sodium citrate and sodium chloride, to a site at which it is desired to prevent adhesion formation. For example, U.S. Pat. Nos. 5,256,408 and 4,968,675 which describe examples of suitable vehicles for aminosteriod lazaroids for topical ophthalmic and parenteral use, respectively. Pursuant to preferred embodiments of the present invention, however, at least one lazaroid compound is administered in a single dose delivery (for example, prior to suturing after surgery) using a drug-delivery system which enables the maintenance of requisite concentrations of the compound for a period of time sufficient for re-epithelialization. A suitable drug-delivery system would itself be essentially inactive (i.e., essentially non-inflammatory and non-immunogenic) and would permit release of the lazaroid compound so as to maintain effective levels thereof over the desired time period.

A large variety of alternatives are known in the art as suitable for purposes of sustained release and are contemplated as within the scope of the present invention. Suitable delivery vehicles include, but are not limited to, the following: microcapsules or microspheres; liposomes and other lipid-based release systems; viscous instillates; absorbable and/or biodegradable mechanical barriers; and polymeric delivery materials, such as polyethylene oxide/polypropylene oxide block copolymers (e.g. poloxamers), poly-orthoesters, cross-linked polyvinyl alcohol, polyanhydrides, polymethacrylate and polymethacryladmide hydrogels, anionic carbohydrate polymers, etc. Useful delivery systems are well known in the art and are described in, e.g., U.S. Pat. No. 4,937,254, the entire disclosure of which is hereby incorporated by reference.

One particularly suitable formulation to achieve the desired near zero-order release of at least one lazaroid compounds such as the compounds of general formulae I or II comprise injectable microcapsules or microspheres prepared from a biodegradable polymer, such as poly(dl-lactide), poly(dl-lactide-co-glycolide), poly-caprolactone, polyglycolide, polylactic acid-co-glycolide, poly(hydroxybutyric acid), a polyortho-ester or a polyacetal. Injectable systems comprising microcapsules or microspheres of a diameter on the order of about 50 to about 500 µm offer advantages over other delivery systems. For example, they generally use less active agent and may be administered by paramedical personnel. Moreover, such systems are inherently flexible in the design of the duration and rate of separate drug release by selection of microcapsule size, drug loading and dosage administered. In addition, such microcapsules can be successfully sterilized with gamma irradiation.

Microcapsules are systems comprising a polymeric wall that encloses a liquid or solid core. The capsule wall usually does not react with the core material; however, it is designed to provide sufficient strength to enable normal handling without rupture while being sufficiently thin to allow a high core to wall volume ratio. The capsule contents remain within the wall until released by diffusion or other means that dissolve, melt, break, rupture or remove the capsule material. Preferably, the capsule wall can be made to degrade and decompose in suitable environments while diffusing the core material through the capsule wall to allow for its slow, prolonged delivery.

The mechanism of release in biodegradable microcapsules is a combination of drug diffusion and polymer biodegradation. Therefore, the rate and duration of release are determined by microcapsule size, drug content and quality, and polymer parameters such as crystallinity, molecular weight and composition. In particular, adjustment in the amount of drug released is generally achieved by modification of capsule wall thickness, capsule diameter, or both. Detailed information concerning the design, preparation and use of microspheres and microcapsules is provided by, e.g., Lewis, D. H., "Controlled Release of Bioactive Agents from Lactide/Glycolide Polymers," in "Biodegradable Polymers as Drug Delivery Systems," Jason & Langer, eds., pp. 1–41 (1990), the entire disclosure of which is hereby incorporated by reference. The sustained intraperitoneal release of dexamethasone using poly(lactide-co-glycolide) microparticles is described in Hoeckel, M. et al., "Prevention of Peritoneal Adhesions in the Rat with Sustained Intraperitoneal Dexamethasone Delivered by a Novel Therapeutic System," *Annales Chirurgiae et Gynaecologiae*, Vol. 76, pp. 306–313

(1987), the entire disclosure of which is also incorporated by reference.

As is well known to those skilled in the art, various methods are currently available for preparing microcapsules, any of which could be employed to provide formulations in accordance with the present invention. Biodegradable polymeric materials suitable for preparation of microcapsules for controlled (i.e., near zero-order) release would be readily determined through routine experimentation by those skilled in the art. Moreover, alternative delivery systems suitable for use in accordance with the present invention (for example, fibers or filaments comprising the active agents) based on biodegradable polymers are also contemplated as within the scope of the present invention.

An alternative approach for the single-dose delivery of at least one lazaroid compound involves the use of biodegradable polymers, such as the ones described above, in the form of a film. Such films may be produced by spraying or discharging dispersed liquid droplets containing the biopolymer and at least one lazaroid in a suitable carrier from a pressurized container onto the targeted site.

Another approach for the single-dose delivery of at least one lazaroid compound, in accordance with the present invention, involves the use of liposomes and other lipid-based delivery systems. The encapsulation of an active agent in multilamellar vesicles (or liposomes) is a well known technique to assist in target drug delivery and prolong drug residence. In a typical procedure, a liposome-forming powdered lipid mixture is added to the desired quantity of active agent in aqueous solution (e.g., phosphate buffered saline) to form a suspension. After a suitable hydration period, the hydrated suspension is then autoclaved to provide the liposome-active agent preparations. A lipid mixture suitable for formation of liposomes may be prepared from L-alpha-distearoyl phosphatidylcholine and cholesterol dissolved in chloroform, to which alpha-tocopherol is added; other compositions and methods for formation of liposomes would, however, also be useful for this purpose. The intraperitoneal administration of liposomes containing ibuprofen or tolmetin is described in Rodgers, K. et al., "Inhibition of Postsurgical Adhesions by Liposomes Containing Nonsteroidal Anti-inflammatory Drugs," *Int. J. Fertil.*, Vol. 35, p. 40 (1990), the entire disclosure of which is hereby incorporated by reference.

Other lipid-based delivery systems are also contemplated for use in this invention. One useful system includes lipid foams such as DepoFoam extended-release formulations comprising spherical particles bounded by a single bilayer lipid membrane and each containing numerous nonconcentric aqueous chambers which encapsulate the active ingredient (see, e.g., Kim, T. K. et al. (1993) "Extended-release formulation of morphine for subcutaneous administration," *Cancer Chemother. Pharmacol.*, Vol. 33, 187; Chatelut, E. et al. (1993) "A slow-release methotrexate formulation for intrathecal chemotherapy," *Cancer Chemother. Pharmacol.*, Vol. 32, 179.] Such lipid particles are made from nontoxic lipids identical to those found in cell membranes.

Yet another suitable approach for single dose delivery of at least one lazaroid compound, in accordance with the present invention involves the use of so-called viscous instillates. In this technique, high-molecular-weight carriers are used in admixture with the active agents, giving rise to an extended structure include, but are not limited to, the following: dextrans and cyclodextrans; hydrogels; cross-linked viscous materials, including viscoelastics and cross-linked viscoelastics; carboxymethylcellulose; and hyaluronic acid. While some studies have suggested that the use of viscous barrier solutions per se may have an advantageous effect in reducing the incidence of adhesion formation, it is believed that any such effect is of limited scope when compared to the combination of at least one lazaroid compound and carrier. The intraperitoneal administration of a viscous instillate comprising rolmerin is described in Abe, H. et al., "The Effect of intra-peritoneal Administration of Sodium Tolmetin-Hyaluronic Acid on the Postsurgical Cell Infiltration In Vivo," *J Surg. Res.*, Vol. 49, p. 322 (1990), the entire disclosure of which is hereby incorporated by reference.

Pursuant to yet another approach, the lazaroid compound is administered in combination with an absorbable mechanical barrier which alone reduces adhesion formation. As would be readily apparent to one working in the field, a lazaroid compound, preferably one of general formulae I or II, may be covalently or non-covalently (e.g., ionically) bound to such a barrier, or it may simply be dispersed therein. A particularly suitable mechanical barrier for use in this particular embodiment of the invention comprises oxidized regenerated cellulose; one such absorbable barrier is available under the designation INTERCEED(TC7) from Johnson and Johnson Medical, Inc., New Brunswick, N.J. [INTERCEED(TC7) Adhesion Barrier Study Group, "Prevention of postsurgical adhesions by INTERCEED(TC7), an absorbable adhesion barrier: a prospective, randomized multicenter clinical study," *Fertility and Sterility*, Vol. 51, p. 933 (1989)]. The use of a mechanical barrier as a carrier to deliver heparin to traumatized surfaces is disclosed in Diamond, M. P. et al., "Synergistic effects of INTERCEED(TC7) and heparin in reducing adhesion formation in the rabbit uterine horn model," *Fertility and Sterility*, Vol. 55, p. 389 (1991) and Diamond, M. P. et al., "Adhesion reformation: reduction by the use of INTERCEED(TC7) plus heparin," *J. Gyn. Surg.*, Vol. 7, p. 1 (1991), the entire disclosures of which are hereby incorporated by reference.

The invention may be better understood with reference to the accompanying examples, which are intended to be illustrative only and should not be viewed as in any sense limiting the scope of the invention, which is defined hereinafter in the accompanying claims.

EXAMPLES

Multiple studies to confirm the efficacy of a lazaroid compound, exemplary compound U83,836e, in the reduction of adhesion formation after peritoneal surgery were performed. Two model systems were employed: the sidewall adhesion model and the uterine horn model. A clear correlation between results obtained using both of these models and utility in adhesion prevention has been demonstrated with INTERCEED(TC7), for which clear clinical efficacy has been shown and FDA approval for adhesion prevention in gynecological surgery has been obtained.

In the peritoneal sidewall model, rabbit were pre-anesthetized with 1.2 mg/kg acetylpromazine and anesthetized with a mixture of 55 mg/kg ketamine hydrochloride and 5 mg/kg xylazine intramuscularly. Following preparation for sterile surgery, a midline laparotomy was performed. A 3×5-cm area of peritoneum and transversus abdominis muscle was removed on the right lateral abdominal wall. The cecum was exteriorized, and digital pressure was exerted to create subserosal hemorrhages over all cecal surfaces. The cecum was then returned to its normal anatomic position. The compound to be tested was placed in an Alzet minoosmotic pump (Alza Corporation, Palo Alto, Calif., USA) to allow continuous release of the molecule through the postsurgical interval. The Alzet miniosmotic pump was placed in the subcutaneous space and a delivery tube connected the pump with the site of injury at sidewall. Vehicle was placed in the pump of control rabbits. The abdominal wall and skin were closed in a standardized manner.

After 7 days, the rabbits were sacrificed and the percentage of the area of the sidewall injury that is involved in adhesions was determined. In addition, the tenacity of the adhesion formed was scored use a system as follows:

```
0 = No adhesions
1 = mild, easily dissectable adhesions
2 = moderate adhesions; non-dissectable, does
    not tear organ
3 = dense adhesions; non-dissectable, tears
    when removed
```

A reduction in the area or the tenacity of the adhesions would be considered beneficial.

In additional experiments, a rabbit uterine horn model was employed. This model has been previously shown to cause severe adhesions in rabbits after surgery [Nishimura, K. et al., "The Use of Ibuprofen for the Prevention of Postoperative Adhesions in Rabbits," *Am. J. Med.*, Vol. 77, pp. 102–106 (1984)]. The rabbits were anesthetized (130 mg/kg ketamine and 20 mg/kg acetylpromazine im) and prepared for sterile surgery. A midline laparotomy was performed, and surgical trauma was performed on both uterine horns by abrading the serosal surface with gauze until puncrate bleeding developed. Ischemia of both uterine horns was induced by removal of the collateral blood supply. After traumatization, the abdominal wall was closed in two layers. The compound to be tested was delivered as described for the peritoneal sidewall model, but the tubing was placed over the injured uterine horns.

With the uterine horn model, an initial score to represent the overall extent of adhesions is given (0 to 4+). The percentage of a surface of the horn involved in adhesions to various organs are given in the tables below the overall adhesion score.

In the model systems employed in the examples reported herein, the exemplary compound U83,836e was shown to reduce the incidence of peritoneal adhesions. In these Examples, drug was delivered at a rate of 10 μl/hour. The concentration ranges employed were 0.06–0.6 mg/ml. For purposes of preventing adhesion formation in accordance with the present invention, it is not believed that high systemic levels of lazaroid compounds would be necessary.

Example 1

The efficacy of lazaroid U83,836e in preventing adhesion formation was evaluated in the sidewall model. The drug was delivered for 7 days at a rate of 10 μl/hr and the animals were sacrificed after 7 days. The vehicle was 0.02 mg/ml citric acid, 0.0032M sodium citrate, and 0.077M NaCl, pH 3.5. Relative to the control, U83,836e was found to be efficacious in adhesion reduction. The results are summarized in Table 1. A student t test analysis of the data was performed and the results are reported in Table 1 as well.

TABLE 1

| Treatment | % Adhesions | Adhesion Score |
|---|---|---|
| Vehicle Control | 50% | 2+[A] |
|  | 80% | 2+[A] |
|  | 80% | 2+ |
|  | 100% | 2+ |
|  | 100% | 3+ |
|  | 90% | 3+ |
| Mean: | 83.3% ± 17 |  |
| 0.6 mg/ml Lazaroid | 0% | 0+ |
|  | 0% | 0+ |
|  | 0% | 0+ |
|  | 0% | 0+ |
|  | 20% | 1+ |
|  | 40% | 1+ |
| Mean[C]: | 10.0% ± 15.28 |  |
| 0.06 mg/ml Lazaroid | 0% | 0+[B] |
|  | 0% | 0+ |
|  | 30% | 1+ |
|  | 70% | 1+ |
|  | 0% | 0+ |
|  | 80% | 1+ |
| Mean[D]: | 30.0% ± 33.17 |  |

[A]: inflammation
[B]: bleeding, inflammation at sidewall
[C]: p = 0.000
[D]: p = 0.006

Example 2

Lazaroid U83,836e was examined in the double uterine horn model for adhesion prevention. The drug was delivered for 7 days at a rate of 10 μl/hour and the animals were sacrificed at day 7. The statistical analysis done on the data from the double uterine horn model (nonparametric data) is done on the overall score. The data is rank ordered, a rank value given and an analysis of variance on the ranks is performed. The results are summarized in Tables 2 and 3.

TABLE 2

| Treatment | Overall Adhesion Score |
|---|---|
| Vehicle Control | 3.5+ |
|  | 2.5+ |
|  | 3+ |
|  | 3+ |
|  | 3.5+ |
|  | 3+ |
| 0.6 mg/ml Lazaroid | 1+ |
|  | 1.5+ |
|  | 1.5+ |
|  | 1.5+ |
|  | 1+ |
|  | 1.5+ |
| 0.06 mg/ml Lazaroid | 1.5+ |
|  | 2.5+ |
|  | 0.5+ |
|  | 1.5+ |
|  | 0.5+ |
|  | 1.5+ |

TABLE 3

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| Control | 40 | 60 | 40 | 60 | 40 | 60 | 40 | 60[b] |
| | 40 | 30 | 20 | 0 | 40 | 30 | 10 | 0[a] |
| | 30 | 80 | 50 | 50 | 30 | 80 | 50 | 50[b] |
| | 40 | 80 | 0 | 30 | 40 | 80 | 0 | 30 |
| | 30 | 100 | 40 | 40 | 30 | 100 | 40 | 40[b] |
| | 20 | 70 | 10 | 10 | 20 | 70 | 30 | 10[b] |
| Mean | 33.3 | 70 | 26.7 | 31.7 | 33.3 | 70 | 28.3 | 31.7 |
| 0.6 mg/ml Lazaroid | 0 | 0 | 10 | 0 | 0 | 10 | 0 | 0[a] |
| | 0 | 0 | 10 | 10 | 0 | 0 | 10 | 10 |
| | 0 | 20 | 0 | 0 | 0 | 20 | 20 | 0 |
| | 0 | 0 | 30 | 20 | 0 | 0 | 30 | 20 |
| | 10 | 0 | 20 | 0 | 10 | 0 | 10 | 0 |
| | 0 | 10 | 0 | 0 | 0 | 10 | 20 | 0 |
| Mean | 1.7 | 5 | 11.7 | 5 | 1.7 | 6.7 | 15 | 5 |
| 0.06 mg/ml Lazaroid | 0 | 20 | 30 | 0 | 0 | 20 | 10 | 0 |
| | 20 | 30 | 10 | 40 | 20 | 30 | 10 | 40[a] |
| | 0 | 0 | 10 | 0 | 0 | 0 | 10 | 0 |
| | 0 | 20 | 10 | 30 | 0 | 0 | 0 | 30 |
| | 0 | 0 | 0 | 0 | 0 | 10 | 0 | 0 |
| | 0 | 10 | 20 | 20 | 0 | 10 | 20 | 20 |
| Mean | 3.3 | 13.3 | 13.3 | 15 | 3.3 | 11.7 | 8.3 | 15 |

[a]Bladder, horn or bowel adhered to the sidewall (at either tube or tube suture)
[b]Horn and bowel or bladder to sidewall Statistical analysis was performed on the overall score of the nonparametric data taken from Table 2. The data was rank ordered and assigned a rank value. Analysis of the variance of the ranks was then performed and the resulting student t test results are summarized below.

| Treatment | Rank order | p value |
|---|---|---|
| Control | 15.4 + 1.72 | — |
| 0.6 mg/ml lazaroid | 6.5 + 2.12 | 0.000 |
| 0.06 mg/ml lazaroid | 6.58 + 3.93 | 0.000 |

Example 3

The efficacy of lazaroid U83,836e in the double uterine horn model was further evaluated in a kinetics study. In this study, the pump was disconnected at various times after surgery to determine the time period of exposure to the drug effective to reduce adhesion formation. The efficacy of the lazaroid in preventing adhesions improved at longer exposure times (72 hours) for the two concentrations tested. The results are summarized in Tables 4 and 5.

TABLE 4

| Treatment | Overall Adhesion Score |
|---|---|
| Vehicle Control | 3.5+ |
| | 2.5+ |
| | 3.5+ |
| | 3.5+ |
| | 3.5+ |
| | 2.5+ |

TABLE 4-continued

| Treatment | Overall Adhesion Score |
|---|---|
| 0.6 mg/ml Lazaroid 24 hour D/C | 3+ |
| | 1+ |
| | 2+ |
| | 2+ |
| | 1.5+ |
| | 1.5+ |
| 0.6 mg/ml Lazaroid 48 hour D/C | 2.5+ |
| | 1.5+ |
| | 1.5+ |
| | 2+ |
| | 1.5+ |
| | 2+ |
| 0.6 mg/ml Lazaroid 72 hour D/C | 1+ |
| | 1+ |
| | 1+ |
| | 1.5+ |
| | 1+ |
| | 1+ |
| 0.06 mg/ml Lazaroid 24 hour D/C | 2.5+ |
| | Died |
| | 1+ |
| | 2.5+ |
| | 1+ |
| | 3+ |
| 0.06 mg/ml Lazaroid 48 hour D/C | 1+ |
| | 1+ |
| | 1.5+ |
| | 1+ |

TABLE 4-continued

| Treatment | Overall Adhesion Score |
|---|---|
|  | 2.5+ |
|  | 1+ |
| 0.06 mg/ml Lazaroid 72 hour D/C | 1.5+ |
|  | 1+ |
|  | 1+ |
|  | 1+ |
|  | 0.5+ |
|  | 1+ |

TABLE 5

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| Control | 40 | 70 | 30 | 50 | 40 | 70 | 30 | 50** |
|  | 40 | 0 | 30 | 60 | 40 | 0 | 30 | 60* |
|  | 60 | 30 | 40 | 70 | 60 | 30 | 60 | 70 |
|  | 80 | 60 | 50 | 40 | 80 | 60 | 30 | 40 |
|  | 40 | 100 | 40 | 50 | 40 | 100 | 40 | 50** |
|  | 20 | 40 | 30 | 0 | 20 | 40 | 30 | 0* |
| Mean | 46.7 | 50 | 36.7 | 45 | 46.7 | 50 | 36.7 | 45 |
| 0.6 mg/ml Lazaroid 24 hr D/C | 100 | 30 | 40 | 0 | 100 | 30 | 30 | 0* |
|  | 10 | 0 | 10 | 10 | 10 | 0 | 0 | 10* |
|  | 30 | 0 | 50 | 0 | 30 | 0 | 10 | 0 |
|  | 0 | 0 | 40 | 20 | 0 | 0 | 20 | 20** |
|  | 10 | 40 | 30 | 0 | 10 | 40 | 0 | 0* |
|  | 0 | 20 | 10 | 10 | 0 | 20 | 10 | 10** |
| Mean | 25 | 15 | 30 | 6.7 | 25 | 15 | 11.7 | 6.7 |
| 0.6 mg/ml Lazaroid 48 hr D/C | 40 | 30 | 20 | 0 | 40 | 30 | 30 | 0 |
|  | 0 | 20 | 30 | 0 | 0 | 20 | 0 | 0* |
|  | 0 | 20 | 40 | 0 | 0 | 0 | 0 | 0* |
|  | 0 | 10 | 50 | 10 | 0 | 10 | 20 | 10** |
|  | 0 | 10 | 30 | 20 | 0 | 10 | 20 | 20 |
|  | 0 | 40 | 30 | 10 | 0 | 40 | 10 | 10** |
| Mean | 6.7 | 21.7 | 33.3 | 6.7 | 6.7 | 18.3 | 13.3 | 6.7 |
| 0.6 mg/ml Lazaroid 72 hr D/C | 0 | 10 | 0 | 0 | 0 | 10 | 30 | 0 |
|  | 0 | 0 | 20 | 20 | 0 | 0 | 20 | 20 |
|  | 0 | 0 | 20 | 10 | 0 | 0 | 10 | 10* |
|  | 10 | 0 | 20 | 10 | 10 | 0 | 10 | 10 |
|  | 0 | 0 | 20 | 30 | 0 | 0 | 20 | 30 |
|  | 0 | 0 | 30 | 0 | 0 | 0 | 10 | 0 |
| Mean | 1.7 | 1.7 | 18.3 | 11.7 | 1.7 | 1.7 | 16.7 | 11.7 |
| 0.06 mg/ml Lazaroid 24 hr D/C | 50 | 0 | 30 | 10 | 40 | 0 | 10 | 10* |
| | DIED D3 P/O | | | | | | | |
|  | 20 | 0 | 30 | 10 | 10 | 0 | 10 | 10* |
|  | 10 | 40 | 40 | 20 | 10 | 40 | 30 | 20** |
|  | 0 | 10 | 40 | 0 | 0 | 10 | 0 | 0 |
|  | 50 | 10 | 30 | 30 | 50 | 10 | 40 | 30 |
| Mean | 26 | 12 | 34 | 14 | 22 | 12 | 18 | 14 |
| 0.06 mg/ml Lazaroid 48 hr D/C | 0 | 20 | 20 | 0 | 0 | 20 | 0 | 0 |
|  | 0 | 20 | 10 | 0 | 0 | 20 | 0 | 0 |
|  | 0 | 30 | 40 | 0 | 0 | 10 | 10 | 0 |
|  | 10 | 0 | 0 | 0 | 10 | 0 | 10 | 0 |

TABLE 5-continued

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| | 20 | 20 | 30 | 0 | 20 | 20 | 10 | 0** |
| | 0 | 10 | 20 | 0 | 0 | 10 | 10 | 0 |
| Mean | 5 | 16.7 | 20 | 0 | 5 | 13.3 | 6.7 | 0 |
| 0.06 mg/ml Lazaroid 72 hr D/C | 10 | 10 | 10 | 0 | 10 | 10 | 30 | 0* |
| | 0 | 10 | 0 | 0 | 0 | 10 | 20 | 0* |
| | 0 | 0 | 30 | 0 | 0 | 0 | 10 | 0 |
| | 0 | 20 | 0 | 0 | 0 | 20 | 10 | 0 |
| | 0 | 0 | 10 | 0 | 0 | 0 | 10 | 0 |
| | 10 | 0 | 0 | 0 | 10 | 0 | 30 | 0* |
| Mean | 3.3 | 6.7 | 8.3 | 0 | 3.3 | 6.7 | 18.3 | 0 |

*Bladder, horn or bowel adhered to the sidewall (at either tube or tube suture)
**Horn and bowel or bladder to sidewall.

Statistical analysis was performed on the overall score of the nonparametric data taken from Table 4 The data was rank ordered and assigned a rank value. Analysis of the variance of the ranks was then performed and the resulting student t test results are summarized below.

| Test System | Time | Rank Score | p value |
|---|---|---|---|
| Control | — | 37.2 + 3.3 | — |
| 0.6 mg/ml lazaroid | 24 | 24.0 + 8.2 | 0.004 |
| | 48 | 25.3 + 4.2 | 0.000 |
| | 72 | 11.5 + 4.5 | 0.000 |
| 0.06 mg/ml lazaroid | 24 | 24.1 + 12.01 | 0.03 |
| | 48 | 15.3 + 8.83 | 0.000 |
| | 72 | 10.1 + 5.98 | 0.000 |

While there have been shown and described the fundamental novel features of the invention, it will be understood that various omissions, substitutions and changes in the form and details illustrated may be made by those skilled in the art without departing from the spirit of the invention. It is the intention, therefore, to be limited only as indicated by the scope of the following claims.

What is claimed is:

1. A method for prevention of formation of adhesions between organ surfaces, comprising administering an effective amount of at least one lazaroid for a period of time sufficient to permit tissue repair.

2. A method according to claim 1 wherein said lazaroid comprises a compound of general formula I:

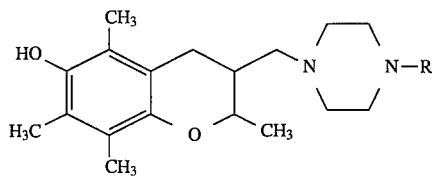

wherein R represents a formula:

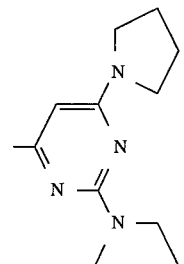

Ia

OR

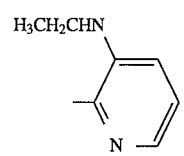

Ib or formula II:

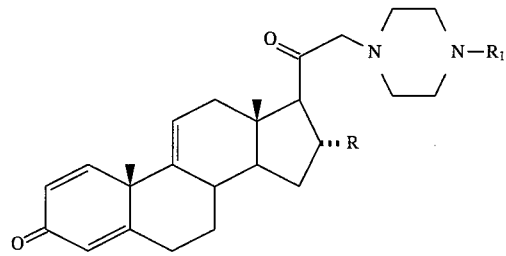

wherein R represents H or $CH_3$; $R_1$ represents formula Ia, as defined above, or formula IIa:

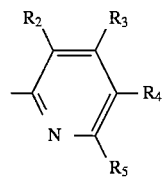

wherein $R_2$, $R_3$, $R_4$, and $R_5$ independently represent H or $NR_6R_7$ wherein $R_6$ and $R_7$ independently represent H and $C_1$-$C_6$ alkyl.

3. A method according to claim 2, wherein the lazaroid comprises: 2-[[4-(2,6-Di-1-pyrrolindinyl-4-pyrimidinyl)-1-piperazinyl] methyl]-3,4-dihydro-2,5,7,8-tetramethyl-2H-1-benzopyran-6-ol, dihydrochloride; (−)-2-[[4-(2,6-Di-1-pyrrolindinyl-4-pyrimidinyl)-1-piperazinyl] methyl]-3,4-dihydro-2,5,7,8-tetramethyl-2H-1-benzopyran-6-ol, 2-hydroxy-1,2,3-propanetricarboxylate; 2H-1-benzopyran-6-ol, 2-[[4-[3-(ethylamino)-2-pyridinyl]-1-piperazinyl]methyl]-3,4-dihydro-2,5,7,8-tetramethyl-, hydrochloride; 2H-1-benzopyran-6-ol, 2-[[4-[3-(ethylamino)-2-pyridinyl]-1-piperazinyl]methyl]-3,4-dihydro-2,5,7,8-tetramethyl-, (Z)-2-butenedioate; 21-[4-[5,6-bis(diethylamino)-2-pyridinyl]-1-piperazinyl]-16-alpha-methyl-pregna-1,4,9(11)-triene-3,20-dione, hydrochloride; 21-[4-[3-ethylamino)-2-pyridinyl]-1-piperazinyl-16-alpha-methyl-pregna-1,4,9(11)-trien-3,20-dione, -(Z)-2-butenedioate; 21-[4-[3-ethylamino)-2-pyridinyl]-1-piperazinyl-16-alpha-methyl-pregna-1,4,9(11)-trien-3,20-dione, hydrochloride; 21-[4-(2,6-di-1-pyrrolidinyl-4-pyrimidinyl)-1-piperazinyl]-16-alpha-methyl)-pregna-1,4,9(11)-triene-3,20-dione monomethanesulfonate; 21-(4-(2,6-di-1-pyrrolindinyl-4-pyrimidinyl)-1-piperazinyl)-pregna-1,4,9(11)-triene-3,20-dione, (Z)-2-butenedioate; 21-(4-(2,6-di-1-pyrrolindinyl-4-pyrimidinyl)-1-piperazinyl)-pregna-1,4,9(11)-triene-3,20-dione, monomethanesulfonate; 16-alpha-methyl-21-[4-[4,6-bis(2-pyridinyl)-1,3,5-triazin-2-yl]-1-piperazinyl]-pregna-1,4,9(11)-triene-3,20-dione, monomethanesulfonate; or 16-alpha-methyl-21-[4-[2,6-bis(2-pyridinyl)-4-pyrimidinyl]-1-piperazinyl]-pregna-1,4,9(11)-triene-3,20-dione, monomethanesulfonate.

4. A method according to claim 1, wherein said lazaroid comprises 2-[(2,6-di-1-pyrrolidinyl)-4-pyrimidinyl-methylaminoethanol or 4-[3-(ethylamino)-2-pyridinyl] piperazine and salts thereof.

5. A method according to claim 1, wherein said tissue repair comprises re-epithelization.

6. A method according to claim 1, wherein said tissue repair comprises mesothelial repair.

7. A method according to claim 1, wherein the lazaroid is administered in conjunction with a delivery vehicle which maintains an effective local concentration at the injury site of said lazaroid compound.

8. A method according to claim 7, wherein said effective local concentration ranges between about 0.007 ng and about 0.033 mg/hr/cm$^2$.

9. A method according to claim 8, wherein said effective local concentration ranges between about 0.007 µg and about 6.7 µg/hr/cm$^2$.

10. A method according to claim 7, wherein said effective local concentration ranges between about 0.04 ng and about 0.2 mg/hr/kg.

11. A method according to claim 10, wherein said effective local concentration ranges between about 0.04 µg and about 40 µg/hr/kg.

12. A method according to claim 1, wherein the lazaroid compound is administered in the form of microcapsules or microspheres.

13. A method according to claim 12, wherein the microcapsules or microspheres comprise a biodegradable polymer selected from the group consisting of poly(dl-lactides), poly(dl-lactide-co-glycolides), polycaprolactones, polyglycolides, polylactic acid-co-glycolides, poly(hydroxybutyric acids), polyortho-esters, polyacetals and mixtures thereof.

14. A method according to claim 1, wherein the lazaroid compound is administered in a form of a film.

15. A method according to claim 14, wherein the film comprises a biodegradable polymer selected from the group consisting of poly(dl-lactides), poly(dl-lactide-co-glycolides), polycaprolactones, polyglycolides, polylactic acid-co-glycolides, poly(hydroxybutyric acids), polyortho-esters, polyacetals and mixtures thereof.

16. A method according to claim 1, wherein the lazaroid compound is administered in the form of liposomes.

17. A method according to claim 16, wherein the liposomes comprise L-alpha-distearoyl phosphatidylcholine.

18. A method according to claim 1, wherein the lazaroid compound is administered in the form of a lipid foam.

19. A method according to claim 1, wherein the lazaroid compound is administered in the form of an instillate.

20. A method according to claim 19, wherein the instillate comprises a high-molecular-weight carrier selected from the group consisting of dextrans, cyclodextrans, hydrogels, carboxymethylcellulose, hyaluronic acid, chondroitin sulfate and mixtures thereof.

21. A method according to claim 1, wherein the lazaroid compound is administered in combination with an absorbable mechanical barrier.

22. A method according to claim 21, wherein the absorbable mechanical barrier comprises oxidized regenerated cellulose.

* * * * *